US009144608B2

(12) United States Patent
Olson et al.

(10) Patent No.: US 9,144,608 B2
(45) Date of Patent: *Sep. 29, 2015

(54) METHOD FOR STIMULATING RETINAL RESPONSE USING PHOTOACTIVE DEVICES

(71) Applicant: The Regents of the University of Colorado, Denver, CO (US)

(72) Inventors: Jeffrey Olson, Cherry Hills, CO (US); Naresh Mandava, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,079

(22) Filed: Apr. 9, 2014

(65) Prior Publication Data
US 2014/0220145 A1    Aug. 7, 2014

Related U.S. Application Data

(63) Continuation of application No. 12/528,832, filed as application No. PCT/US2008/055332 on Feb. 28, 2008, now Pat. No. 8,725,266.

(60) Provisional application No. 60/891,978, filed on Feb. 28, 2007.

(51) Int. Cl.
A61N 1/05 (2006.01)
A61N 1/36 (2006.01)
A61K 41/00 (2006.01)
A61K 9/00 (2006.01)
A61K 33/24 (2006.01)
(Continued)

(52) U.S. Cl.
CPC .............. *A61K 41/00* (2013.01); *A61K 9/0009* (2013.01); *A61K 9/0051* (2013.01); *A61K 33/24* (2013.01); *A61K 33/30* (2013.01); *A61K 41/0004* (2013.01); *A61N 1/0543* (2013.01); *A61N 1/36046* (2013.01); *B82Y 5/00* (2013.01); *Y10S 977/774* (2013.01); *Y10S 977/925* (2013.01)

(58) Field of Classification Search
CPC ............ A61N 1/0543; A61N 1/36046; A61N 2005/0648; B82Y 5/00; Y10S 977/774; Y10S 977/925; Y10S 977/904
See application file for complete search history.

(56) References Cited

U.S. PATENT DOCUMENTS 7,139,612 B2   11/2006   Chow et al.
8,388,668 B2    3/2013   Peyman
8,409,263 B2    4/2013   Peyman
(Continued)

FOREIGN PATENT DOCUMENTS

WO   2004004927   1/2004
WO   2005018681   3/2005
WO   2005041747   5/2005

OTHER PUBLICATIONS

Examination Report in EP Application No. 08730992.8 dated Jun. 4, 2014.

(Continued)

Primary Examiner — Tammie K Heller
(74) Attorney, Agent, or Firm — Snell & Wilmer L.L.P.

(57) ABSTRACT

An improved method for stimulating electrical activity in an eye is provided. Provided is a technique for implanting small, nanometer-sized photoactive devices into an eye to improve electrical activity within an eye or mitigate degradation of electrical response in damaged eyes.

13 Claims, 12 Drawing Sheets

(51) Int. Cl.
*A61K 33/30* (2006.01)
*B82Y 5/00* (2011.01)

(56) References Cited

U.S. PATENT DOCUMENTS

| | | | |
|---|---|---|---|
| 8,460,351 | B2 | 6/2013 | Peyman |
| 2002/0147442 | A1 | 10/2002 | Shadduck |
| 2003/0022374 | A1 | 1/2003 | Greenbaum et al. |
| 2003/0022831 | A1* | 1/2003 | Rothbard et al. ............. 514/12 |
| 2005/0090874 | A1 | 4/2005 | Wu et al. |
| 2005/0136258 | A1 | 6/2005 | Nie et al. |
| 2006/0129210 | A1 | 6/2006 | Cantin et al. |
| 2006/0204441 | A1 | 9/2006 | Atala et al. |
| 2006/0287660 | A1 | 12/2006 | Syed et al. |
| 2007/0028928 | A1 | 2/2007 | Peyman |
| 2008/0220982 | A1 | 9/2008 | Vu |
| 2008/0221645 | A1 | 9/2008 | Kennedy et al. |
| 2008/0241071 | A1 | 10/2008 | West et al. |

OTHER PUBLICATIONS

Final Office Action dated Jan. 9, 2014 in U.S. Appl. No. 12/528,832.
Office Action dated Sep. 6, 2013 in U.S. Appl. No. 12/528,832.
Advisory Action dated Jul. 23, 2013 in U.S. Appl. No. 12/528,832.
Final Office Action dated May 17, 2013 in U.S. Appl. No. 12/528,832.
Office Action dated Dec. 18, 2012 in U.S. Appl. No. 12/528,832.
Office Action dated Oct. 11, 2013 in Canadian Application No. 2,716,991.
Office Action dated Dec. 13, 2012 in U.S. Appl. No. 13/144,277.
Final Office Action dated Apr. 11, 2013 in U.S. Appl. No. 13/144,277.
Hirsch et al., "Nanoshell-mediated near-infrared thermal therapy of tumors under magnetic resonance guidance", Proceedings of the National Academy of Sciences, vol. 100, No. 23, p. 13549-13554 (2003).
Pappas et a., "Nanoscale Engineering of a Cellular Interface with Semiconductor Nanoparticle Films for Photoelectric Stimulation of Neurons", Nano Letters, vol. 7, No. 2, p. 513-519 (2007).
Choi et al., "Quantum dot-induced cell death involves Fas upregulation and lipid preoxidation in human neuroblastoma cells", Journal of Nanobiotechnology, vol. 5, p. 1-13 (2007).
International Search Report and Written Opinion dated Sep. 6, 2010 in Application No. PCT/US2010/020815.
International Preliminary Report on Patentability dated Jul. 19, 2011 in Application No. PCT/US2010/020815.
Office Action dated Mar. 9, 2012 in Canadian Patent Application No. 2,716,991.
Office Action dated Jan. 17, 2013 in Canadian Patent Application No. 2,716,991.
First Examination Report dated Sep. 10, 2012 in European Patent Application No. 08 730 992.8-2112.
Result of Consultation dated Oct. 4, 2012 in European Patent Application No. 08 730 992.8-2112.
Evident Technologies, EviTag Luminescent Labels, Quantum Dot EviTags, "Unique Optical Properties and Biological, Flexible Surfaces to Enable New Life Science Research" dated Mar. 2005, Specification Sheet.
Extended Search Report and Preliminary Opinion dated Nov. 17, 2011 in European Application No. 08730992.8.
Akerman, et al., "Nanocrystal Targeting in Vivo," Proceedings of the National Academy of Sciences of USA, National Academy of Science , Sep. 16, 2002, pp. 12617-12621, vol. 99, No. 20, Washington DC.
Goldman, E. et al., "Avidin: A Natural Bridge for Quantum Dot-Antibody Conjugates," J.AM. CHEM. SOC., vol. 124, Issue 22, Jun. 5, 2002, pp. 6378-82; especially Abstract; p. 6378, paragraph 1; p. 6380, paragraph 5; Fig. 1a.
International Search Report dated Aug. 20, 2008 in Application No. PCT/US2008/055332.
International Preliminary Report on Patentability dated Sep. 11, 2009 in Application No. PCT/US2008/055332.

* cited by examiner

METHOD FOR STIMULATING RETINAL RESPONSE USING PHOTOACTIVE DEVICES

CROSS-REFERENCE TO RELATED APPLICATIONS

This application is a continuation of, and the claims the benefit of, U.S. application Ser. No. 12/528,832, issued May 13, 2014 as U.S. Pat. No. 8,725,266, which is a U.S. national phase filing under 35 U.S.C. §371 of PCT/US2008/55332, filed on Feb. 28, 2008, which claims priority from U.S. Provisional Application No. 60/891,978, filed on Feb. 28, 2007. All of the aforementioned applications are included herein by reference.

FIELD OF INVENTION

The present invention generally relates to use of devices to stimulate retinal response within an eye and reduce or prevent degradation of retinal response in eyes, and more particularly, the invention relates to use of quantum dot devices to induce electrical stimulation of the retina.

BACKGROUND OF THE INVENTION

Many people suffer from various forms of retinal damage, such as retinitis pigmentosa, retinal detachment, diabetic retinopathy, and macular degeneration, which can lead to diminished sight and blindness. And, as the age of the general population increases, the number of people suffering from diminished sight due to these causes increases.

Several devices have been developed to attempt to restore vision loss due to retinal damage. For example, silicon-chip based photovoltaic devices, which are attached to a portion of a retina, have been developed to stimulate rods and cones within the retina. Although such devices may provide some stimulation, the devices suffer from several drawbacks. In particular, the devices are relatively large (e.g., on the order of square millimeters). As a result, when placed on a retina, the devices block significant portions of light that would otherwise reach rods and cones located behind the devices. Another problem associated with these devices is that they are placed on a surface of the retina, which is delicate; thus, the retina surface may tear or otherwise become damaged when the devices are attached to the retina.

Other, silicon-chip based devices, which are implanted subretinally have also been developed to attempt to improve vision in those suffering from retinal damage. Mild improvement of electrical response to light has been observed using these devices. However, several problems have also been observed. Specifically, because the devices are relatively large, once the devices are attached to the retina, oxygen is blocked from reaching cells adjacent to or proximate the devices. In addition, implantation of the devices is thought to further damage the retinal tissue.

Accordingly, improved devices and methods for increasing electrical stimulation of photoreceptors and/or other portions of a retina within an eye are desired.

SUMMARY OF THE INVENTION

The present invention provides an improved method for stimulating electrical activity in an eye. More particularly, the invention provides a technique for implanting small, nanometer-sized photoactive devices to stimulate electrical activity within an eye and mitigate degradation of electrical response in damaged retinas.

While the ways in which the present invention addresses the disadvantages of the prior art will be discussed in greater detail below, in general, the present invention provides a method for measurably increasing electrical response of an eye to light using non-obtrusive devices, while preserving the neural network.

In accordance with one exemplary embodiment of the invention, a method for stimulating an electrical response of a retina includes injecting nano-scale, light-sensitive devices within a vitreous portion of an eye.

In accordance with another embodiment of the invention, a method for stimulating electrical activity of a retina includes injecting a plurality of photoactive devices in a sub-retinal portion of the eye.

In accordance with various embodiments of the invention, the photoactive devices include a quantum dot or nanocrystal. In accordance with various aspects of the exemplary embodiments, the quantum dot fluoresces in the presence of light. In accordance with additional aspects, the quantum dot changes potential upon application of light of certain wavelengths. In accordance with further aspects, a plurality of quantum dots, which produce a change in potential in response to different wavelengths, are used to stimulate electrical activity within an eye. Using quantum dots offers several advantages over prior-art techniques, because the quantum dot devices are much smaller (on the order of nanometers) than traditional chip-based devices used to stimulate retinal electrical response to light.

In accordance with further embodiments of the invention, the photoactive devices are coated with a biocompatible material. In accordance with exemplary aspects of these embodiments, the biocompatible material is a bio-targeted material, configured to adhere to native retinal cells (e.g., ganglia, bipolar cells, or photoreceptor cells) and maintain a close interaction with these cells for an extended period of time.

BRIEF DESCRIPTION OF THE FIGURES

The exemplary embodiments of the present invention will be described in connection with the appended drawing figures in which like numerals denote like elements and.

Skilled artisans will appreciate that elements in the figures are illustrated for simplicity and clarity and have not necessarily been drawn to scale. The dimensions of some of the elements in the figures may be exaggerated relative to other elements to help to improve understanding of embodiments of the present invention.

DETAILED DESCRIPTION OF EXEMPLARY EMBODIMENTS

The present invention provides an improved method for stimulating an electrical response in an eye and mitigating degradation of electrical response to light of an eye having a damaged retina. The method of the present invention may be used with a retina that is damaged due to retinitis pigmentosa, diabetic retinopathy, macular degeneration, retinal detachment, or other retinal trauma and may be implemented on any animal, having an eye with the general properties described herein.

Figure 1:
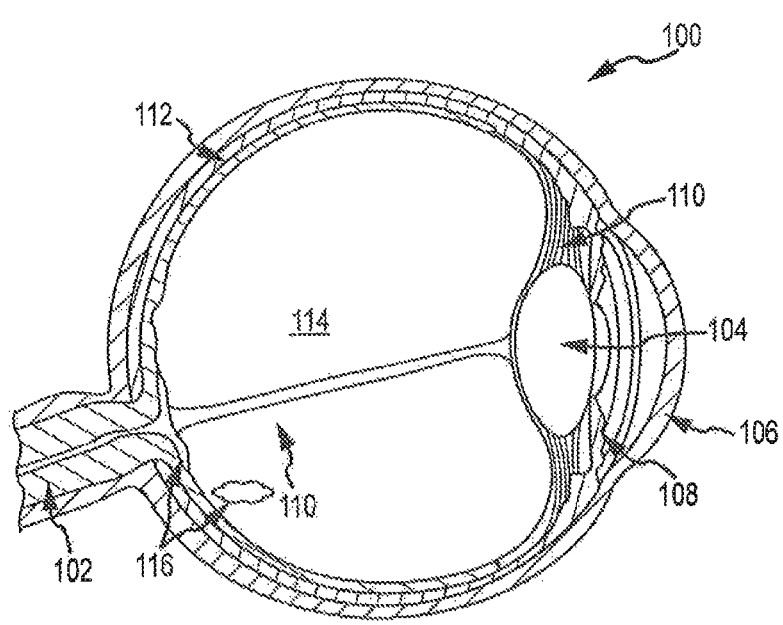
FIG. 1 illustrates an eye and exemplary injection points for photoactive devices, in accordance with various embodiments of the present invention.

FIG. 1 illustrates a mammal eye 100, which includes an optic nerve 102, a lens 104, a cornea 106, an iris 108, zonules 110, a retina 112, and a vitreous 114. In accordance with various embodiments of the invention, photoactive material 116 is injected into eye 100, e.g., using a hypodermic needle, such that the photoactive material is dispersed within vitreous 114 and proximate retina 112. In accordance with alternative embodiments of the invention, photoactive material 116 is injected subretinally.

Figure 2:
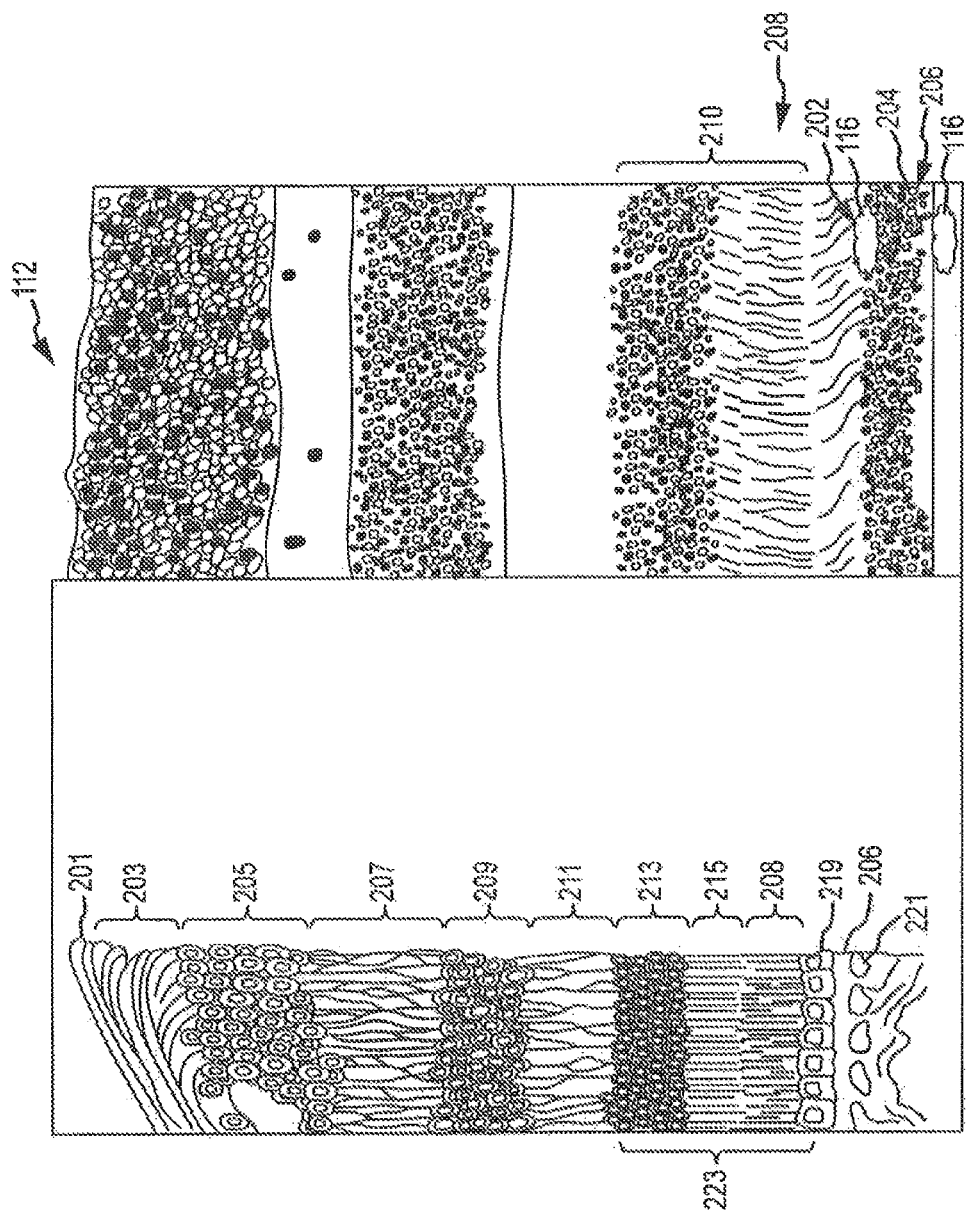
FIG. 2 illustrates a portion of a retina with injected photoactive material in greater detail, in accordance with various embodiments of the invention.

FIG. 2 illustrates a portion of retina 112 in greater detail, illustrating possible injection sites and resting sites for photoactive material 116. The retina includes Internal limiting member 201, nerve-fiber layer 203, ganglion-cell layer 205, inner plexiform layer 207, inner nuclear layer 209, outer plexiform layer 211, outer nuclear layer 213, inner segments 215, outer segments 208, Bruch's membrane 206, RPE 219, and Choriocapillaris 221.

As noted above, photoactive material 116 may be placed on a surface 202 of retina 112 or in a subretinal area 204, such as a space located between a Bruch's membrane 206 and outer segments 208. Photoactive material 116 may be placed directly in such locations, or, as described in more detail below, the material may be coated with a bio-targeted material, which adheres to particular cells, such as ganglia or bipolar cells or photoreceptors 223.

In accordance with various embodiments of the invention, photoactive material 116 includes a quantum dot. A quantum dot is a semiconductor nanostructure that confines motion of conduction band electrons, valence band holes, or excitons (pairs of conduction band electrons and valence band holes) in three spatial directions. The confinement can be due to electrostatic potentials (generated by external electrodes, doping, strain, impurities), due to the presence of an interface between different semiconductor materials (e.g. in the case of self-assembled quantum dots), due to the presence of the semiconductor surface (e.g. in the case of a semiconductor nanocrystal), or any combination thereof. Dimensions of quantum dots are typically on the order of about 1 to about 100 nanometers, and typically about 10 to about 50 nanometers for self-assembled quantum dots.

The quantum dots fluoresce, emit an electrical potential or current, or a combination thereof, when exposed to light. The electrical potential is thought to stimulate rods and cones or other portions of retina 112. The color of fluorescence and properties of the electrical potential general depend on the shape, size, and materials used to form the quantum dot.

Quantum dots for use with the present invention may be formed using a variety of techniques. For example, the quantum dots may be formed by creating a region of a first material having a first bandgap surrounded by a second material of a second bandgap, wherein the second bandgap is larger than the first bandgap. For example, a quantum dot may include a cadmium selenide (CdSe) core surrounded by a zinc selenide (ZnS) shell.

Alternatively, self-assembled quantum dots nucleate spontaneously under certain conditions during molecular beam epitaxy (MBE) and metallorganic vapor phase epitaxy (MOVPE), when a material is grown on a substrate to which it is not lattice matched. The resulting strain between the grown layer and the substrate produces coherently strained islands on top of a two-dimensional "wetting-layer." The islands can be subsequently surrounded by a shell to form the quantum dot.

Individual quantum dots can also be created from two-dimensional electron or hole gases present in remotely doped quantum wells or semiconductor heterostructures. In this case, a surface is coated with a thin layer of photoresist. A lateral pattern is then defined in the resist by electron beam lithography. This pattern can then be transferred to the electron or hole gas by etching, or by depositing metal electrodes (lift-off process) that allow the application of external voltages between the electron gas and the electrodes.

Quantum dots may also be formed in quantum well structures due to monolayer fluctuations in the well's thickness.

Figure 3:
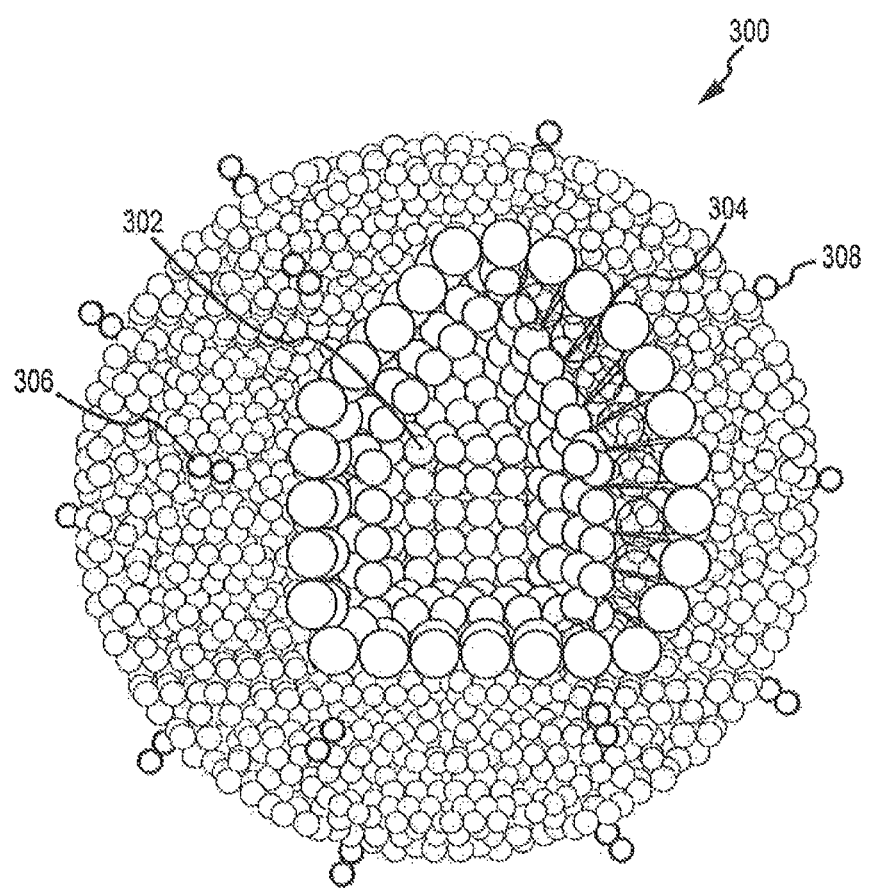
FIG. 3 illustrates an exemplary quantum dot suitable for use in accordance with various embodiments of the invention.

FIG. 3 illustrates a quantum dot 300 suitable for use as photoactive material 116. Quantum dot 300 includes an inner semiconductor 302 core formed of, for example, indium/gallium/phosphide, silicon, gallium arsenide, cadmium telluride, copper indium gallium selenide, indium gallium nitride, or organic materials such as polymer-fullerene heterojunctions (e.g., P3HT+$C_{60}$), organic nanocrystal solar cells (e.g., cadmium selenide or cadmium telluride), dye sensitized cells (e.g., dye and titanium oxide or nobelium oxide), or a tandem cell (e.g., copper-phthalocyanin+$C_{60}$); a shell 304, formed of, for example, zinc selenide or other suitable material; a coating 306, formed of, for example, PEG lipids or other suitable material; and bio-functional material 308, formed of, for example, biotin or other suitable proteins.

As noted above, in accordance with various embodiments of the invention, a plurality of quantum dots exhibiting a plurality of fluorescence wavelengths or dots responsive to light of varying wavelengths are employed to stimulate photoreceptors based on incident light of multiple wavelengths. For example, a combination of nanoparticles responsive to red, blue, and green incident light may be employed. Various other combinations of nanoparticles/quantum dots are also within the scope of the invention.

Use of photoactive nanoparticles such as quantum dots is advantageous because it allows for less invasive methods of implanting the devices, which in turn minimizes trauma and scaring of the retina. In addition, because the particles are so small, the particles block relatively little light from photoreceptors 210 (illustrated in FIG. 2). Further, the quantum dots can be injected into a wider field of vision, compared to larger devices.

FIGS. 4-7 illustrate electroretinograms (ERG) for Royal College of Surgeons (RCS) rats with retinal degeneration, injected in vitreous 114 with about 5 µl of quantum dots 300 in saline, for a sham group, and for a control group. Intravitreal injections: 0.5 µl injected 1 mm posterior to limbus; subretinal injection: 0.1 µl injected under direct visualization subretinally.

Figure 4:
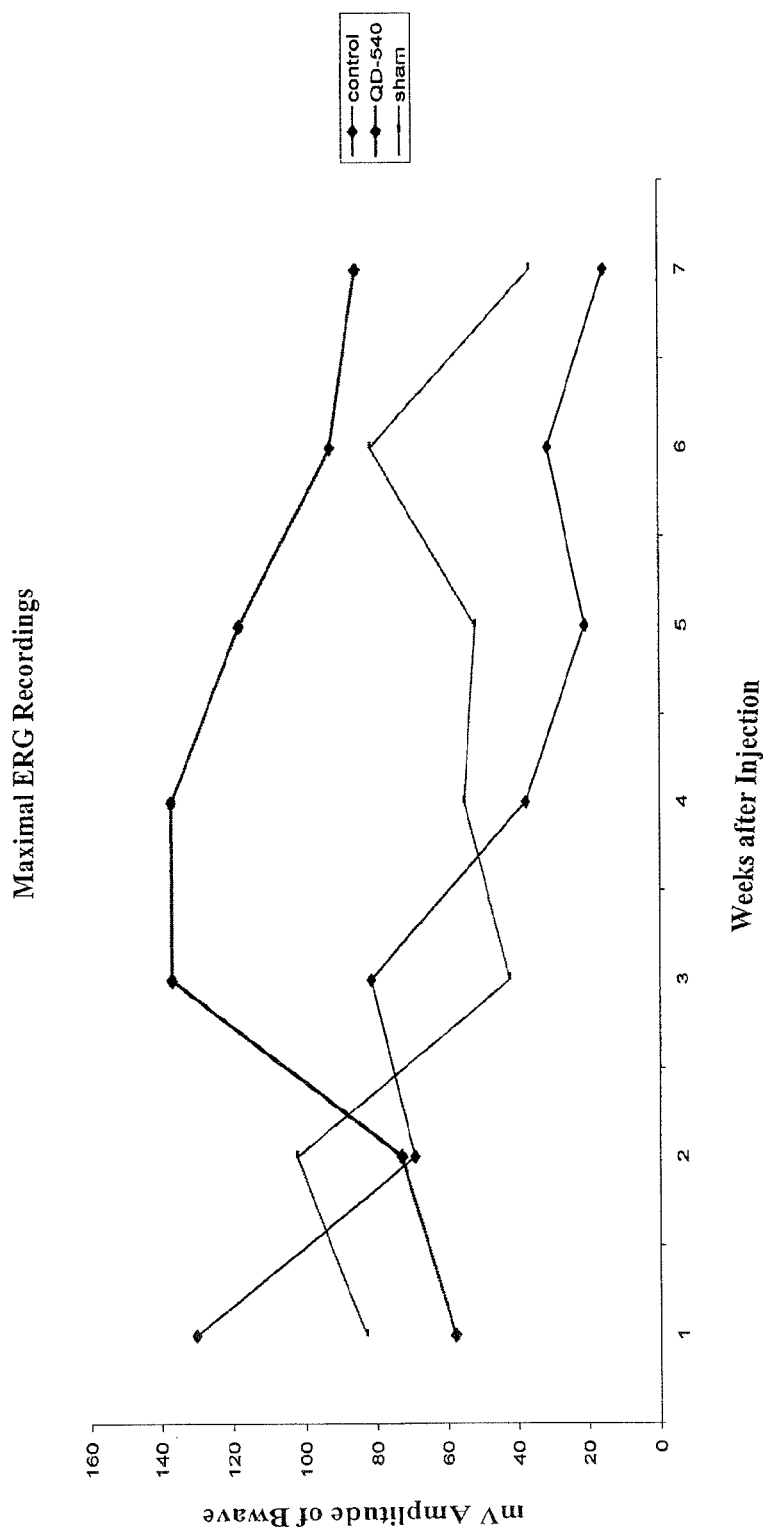
FIGS. 4-7 illustrate electroretinogram (ERG) measurements in control groups and rats injected with photoactive devices in accordance with the invention.

FIG. 4 illustrates maximal dark-adapted ERG, which elicits both rod and cone photoreceptor response, in RCS rats. The control group (n=4) has had no intervention, the sham group (n=4) has received intraocular injections of saline, and the QD-540 group (n=6) has received intraocular injections of quantum dots with a biotin coating. FIG. 4 illustrates an increase in the electrical activity of the active implant eyes in weeks 3 through 7, compared to the sham and control groups, which progressively decline.

Figure 5:
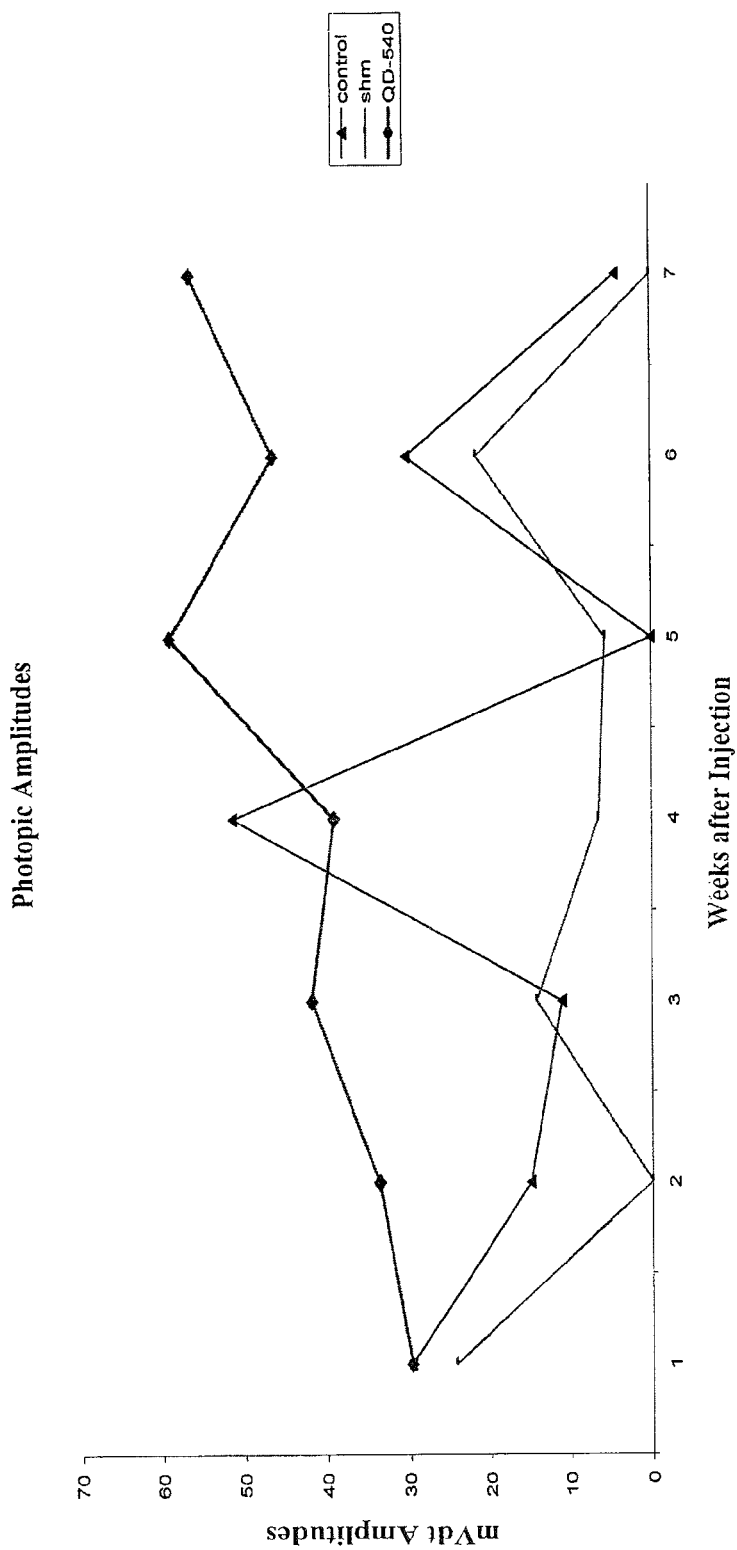

FIG. 5 illustrates photopic light-adapted ERG results, which elicit predominantly cone photoreceptor responses, in the RCS rats. The control group (n=4) has had no interventions, the sham group (n=4) has received intraocular injections of saline, and the QD-540 group (n=6) has received intraocular injections of quantum dots with a biotin coating. FIG. 5 demonstrates a general trend for increasing electrical activity in the active implant group, compared with a tendency for decline in the sham and control groups over time.

Figure 6:
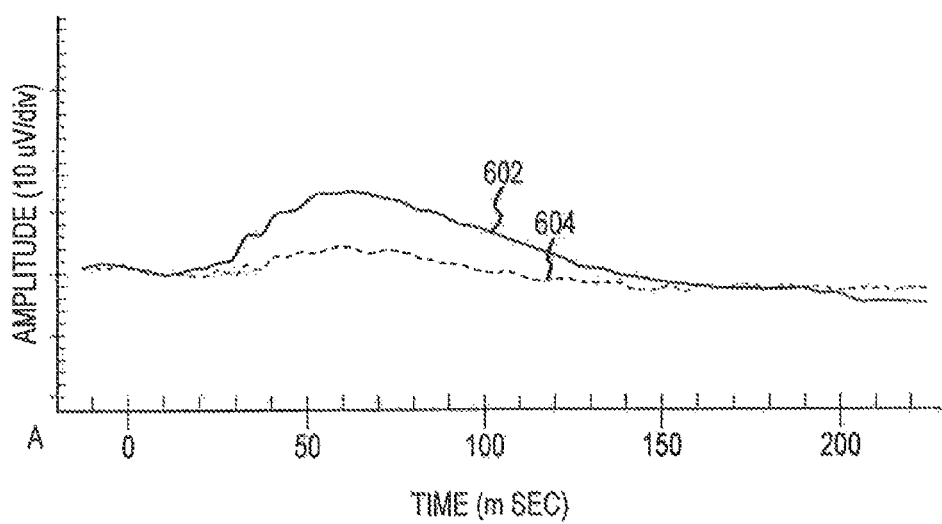
Figure 7:
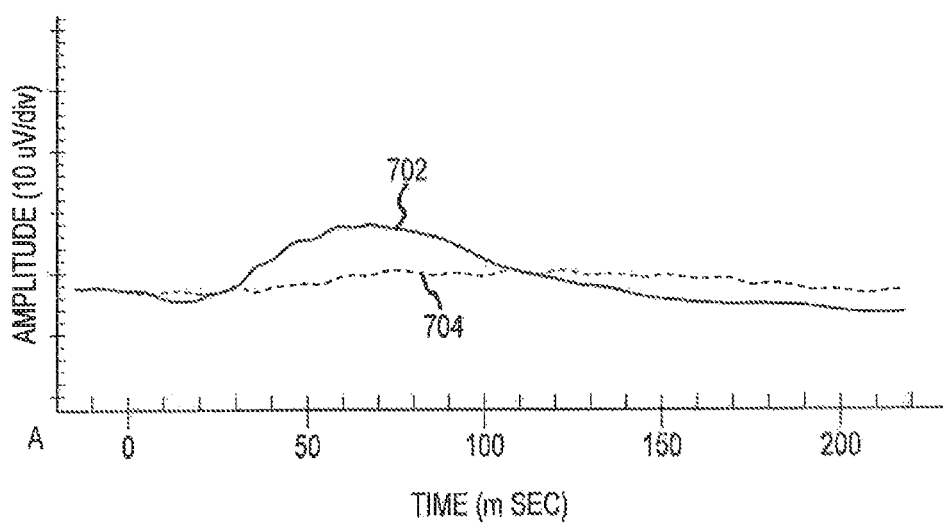

FIG. 6 illustrates ERG recordings week 3 after injection. Line 602 indicates the ERG of an RCS rat with intraocular QD-540, compared with recordings from a representative sham surgery eye, illustrated by line 604. FIG. 7 illustrates representative ERG recordings at week 7. Line 702 indicates the ERG of an RCS rat with intraocular QD-540, compared with recordings from a representative sham surgery eye, represented by line 704. As illustrated, although the overall ERG amplitudes for both sham and injected eyes have decreased, the eye with the active implants has maintained a relatively normal ERG, whereas the sham eye recording is essentially flat.

Figure 8:
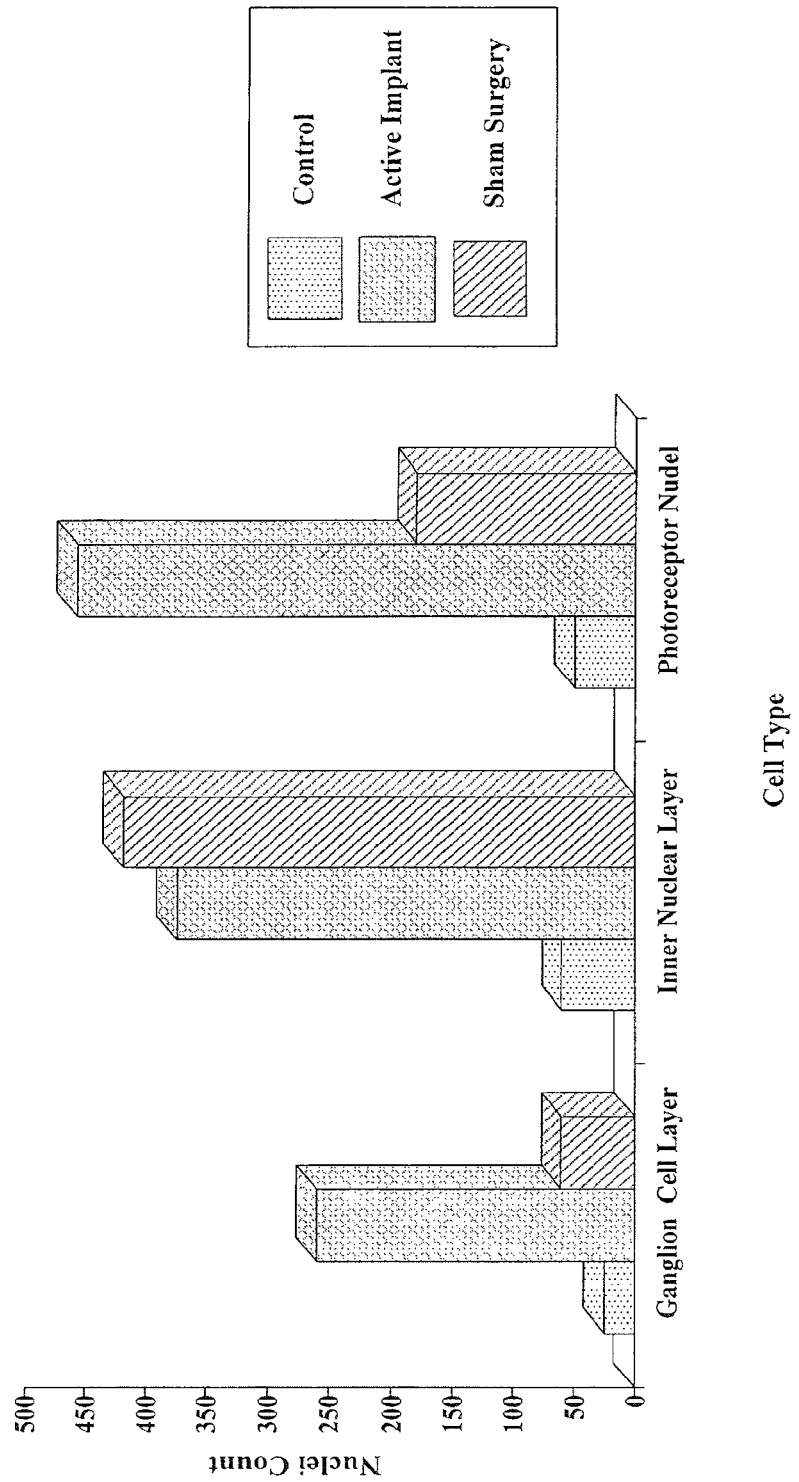
FIG. 8 illustrates nuclei count in ganglion cell layers, inner nuclear layers, and photoreceptor nuclei for control sham, and active groups.

FIG. 8 illustrates nuclei count following a 2 month post-implantation ERG recording.

The RCS rats then were euthanized and the eyes enucleated and the retina embedded in a plastic medium, then cut to 0.5 micron thickness and stained with toludine blue. Using image analysis software, the number of nuclei present in the ganglion cell layer, inner nuclear layer, and the photoreceptor nuclear layer (outer nuclear layer) were measured on five sections each 100 microns in length. There were three animals in the active implant group, 2 in the sham surgery group, and 1 in the control group.

FIG. 8 shows no appreciable difference between the groups in the number of cells present in the ganglion cell layer, a trend for increased cells for both the active implant and sham surgery groups in the inner nuclear layer, and a marked increase in the photoreceptor nuclei in the active implant group. The photoreceptors are the basis of the electrophysiologic network of signals which produce the sensation of vision. Increased numbers of cells in this layer in the active implant group indicates a protective effect of the active implant on these cells. This is consistent with FIGS. 4-7, which depict a preservation of the electrical functioning of the retina in the active implant groups. The intraocular quantum dots appear to preserve both the function and the anatomy of the retina in this model of progressive blindness.

Figure 9:
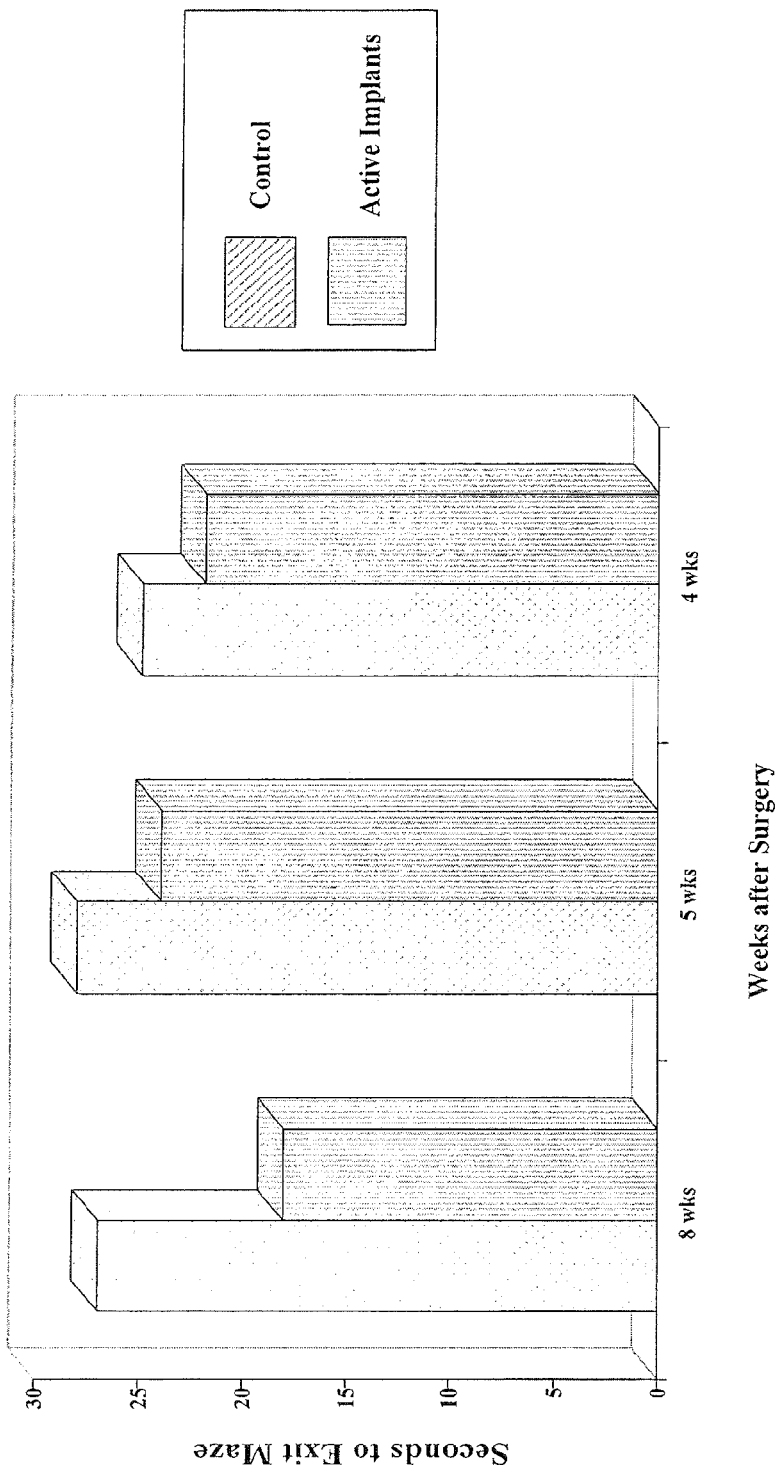
FIG. 9 illustrates Morris Water Maze Test results for control and active groups.

FIG. 9 illustrates results of the Morris Water Maze Test results for three groups. Each group, consisting of one control animal and one active implant animal, was tested in a water maze. The Morris Water Maze Test is a functional test to determine whether or not the animal can see light. The test consists of a water escape pool (1.4 m diameter, 0.6 m deep, water at 20 deg Celsius). Around the edge of the pool are six lights. The escape platform, a small pedestal approximately 12 cm in diameter, is randomly placed adjacent to one light, which is then illuminated as the rat is placed in the water. The subject then has 60 seconds to swim towards the light and climb up onto the pedestal. If the subject does not find the pedestal within 60 seconds, the animal is removed from the pool. Each animal is tested a total of ten times.

In the group of animals 8 weeks post-implantation, the active implant animal was able to escape an average of 30% faster than the control animal. In the 5 week post-implantation group, the active implant group escaped an average 13% more rapidly than the control group and in the 4 week post-implantation group, the active implant had escape times 15% faster than the control.

The results indicate that the animals receiving the active implant were consistently able to navigate the maze more rapidly than the control animals. The maze is specifically designed to eliminate any tactile or olfactory cues, and the animal must rely entirely upon sight to successfully exit.

Figure 10:
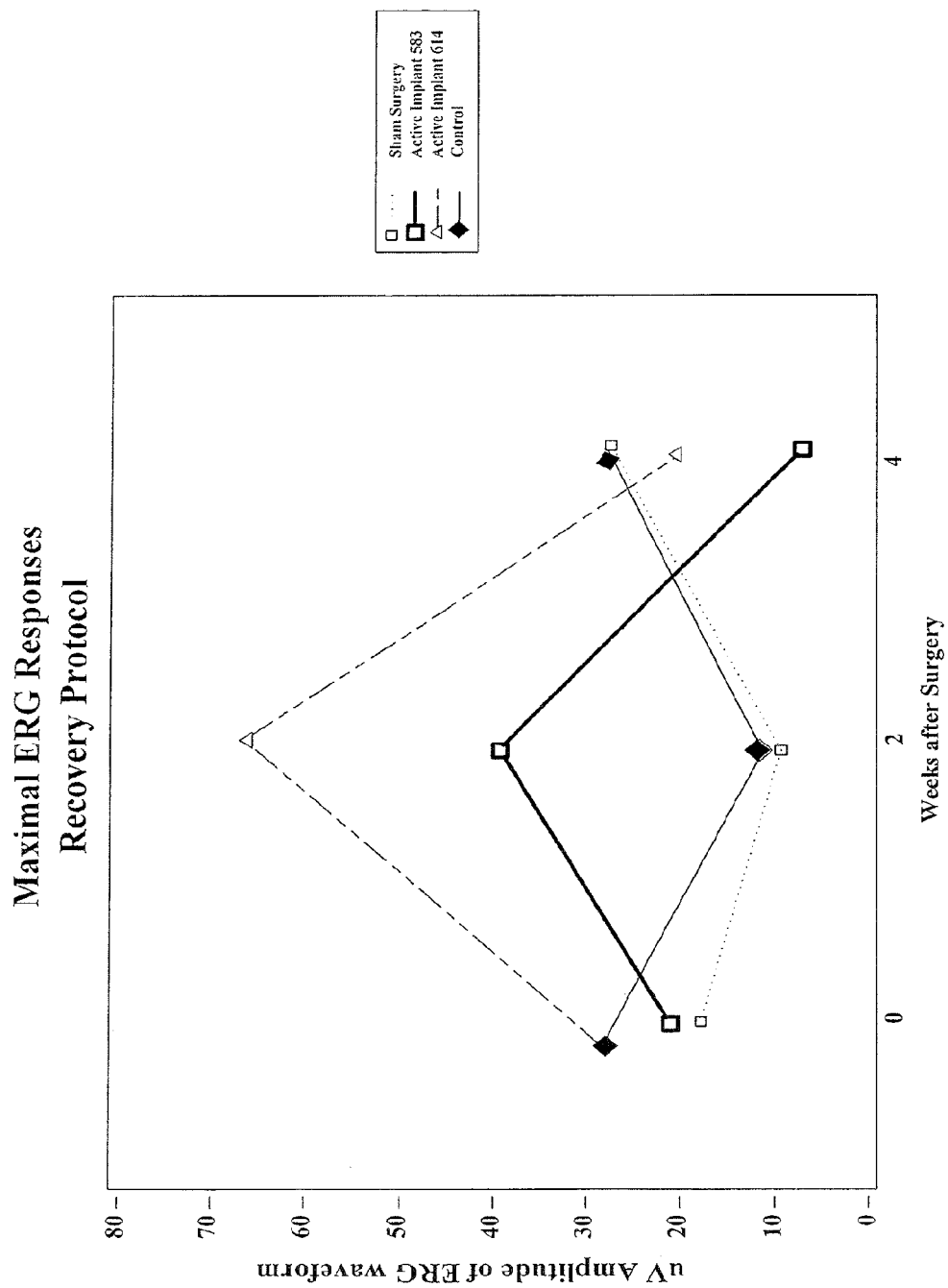
FIG. 10 illustrates Recovery Round, Maximal dark-adapted ERG results for active, sham, and control groups.

FIG. 10 illustrates Recovery Round, Maximal dark-adapted ERG in RCS rats. This test elicits both rod and cone photoreceptor response. FIG. 10 illustrates results from experiments involved in the intraocular injection of quantum dots to reverse blindness. The RCS rats were monitored with electroretinograms every other week until the recordings became essentially flat, indicating a loss of retinal functioning. The control group (n=2) has had no intervention, the sham group (n=2) has received intraocular injections of saline, while Groups Active Implant 593 (n–2) and Active Implant 614 (n=2) have received intraocular injections of quantum dots with an amino acid coating. 593 and 614 refer to the wavelength of light to which each quantum dot exhibits a maximum response. Recordings were taken the day of surgery, 2 weeks post-implantation and 4 weeks post-implantation.

The graph illustrates that both the control and sham surgery groups exhibit no gain in the electrical functioning of the retina at any point post-operatively. In contrast, both active implant groups had a substantial increase in the electrical activity of the retina post-implantation. The Active Implant 593 group had a 2-fold increase in the amplitude of the waveform response to light, and the Active Implant group 614 had a 2.5-fold increase in the amplitude of the waveform response to light.

Figure 11:
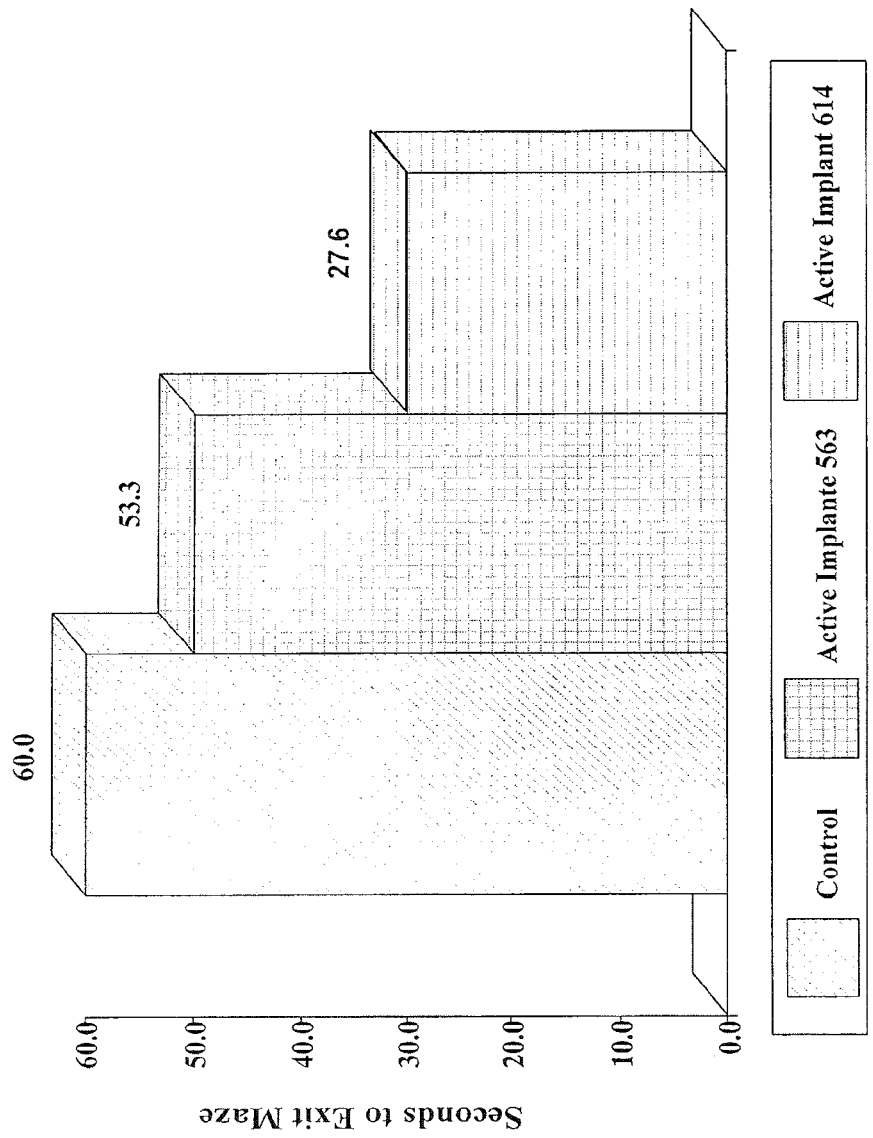
FIG. 11 illustrates Morris Water Maze Test results for control and active groups.

FIG. 11 illustrates Morris Water Maze Test, Recovery Round results for three groups, each group consisting of one representative animal, tested in a water maze. The test consists of a water escape pool (1.4 m diameter, 0.6 m deep, water at 20 deg Celsius). Around the edge of the pool are six lights. The escape platform, a small pedestal approximately 12 cm in diameter, is randomly placed adjacent to one light, which is then illuminated as the rat is placed in the water. The subject then has 60 seconds to swim towards the light and climb up onto the pedestal. If the subject does not find the pedestal within 60 seconds, the animal is removed from the pool. Each animal is tested a total of ten times.

The graph indicates that the control group averaged 60 seconds, indicating that the maze was never successfully completed. The Active Implant 593 group averaged 50 seconds, 17% quicker escape time than control. The Active Implant 614 group averaged 27.6 seconds, nearly twice as fast as the control group, indicating a higher level of visual functioning.

The results indicate that the animals receiving the active implant were consistently able to navigate the maze more rapidly than the control animals. The maze is specifically designed to eliminate any tactile or olfactory cues, and the animal must rely entirely upon sight to successfully exit.

Figure 12:
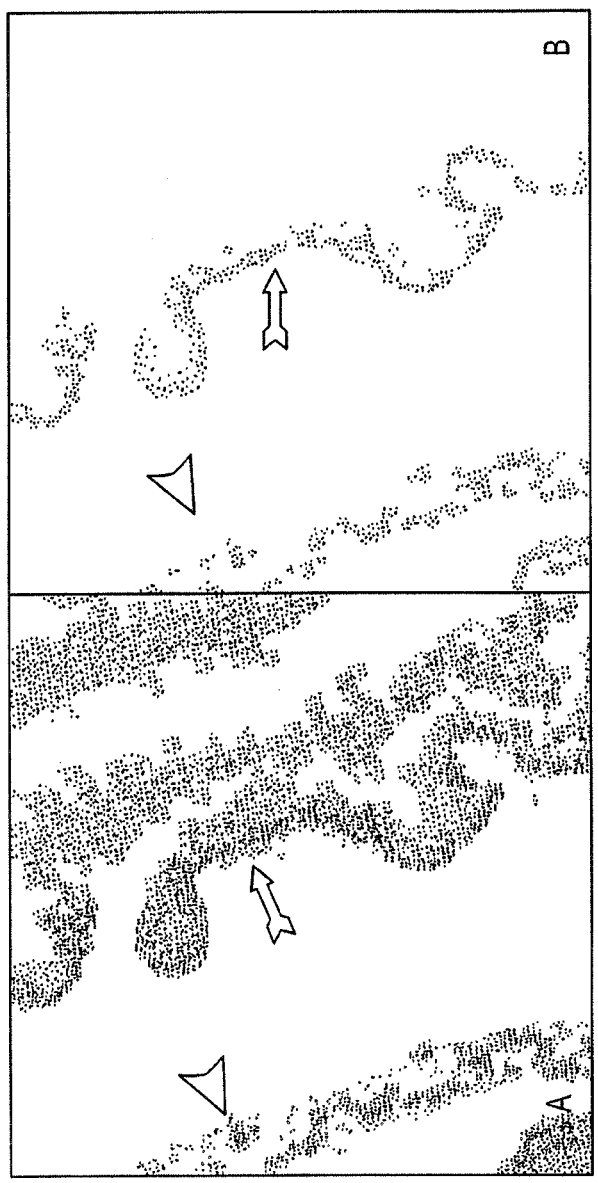
FIG. 12 illustrates photomicrographs of a human retina.

FIG. 12 illustrates photomicrograph of a human retina (A), and quantum dots adherent to human retinal photoreceptors (B). A whole human eye was obtained from the Rocky Mountain Lions Eye Bank and examined grossly and beneath an operating microscope and found to be free of any structural abnormalities. Next, 0.05 ml of a biotin linked quantum dot with an absorption wavelength near 528 nm and an excitation wavelength of 547 nm was injected into the subretinal space. After histological processing, the biotin linked quantum dots were visible by fluorescent light microscopy. The quantum dots could be seen adherent to the native photoreceptors (arrow), as well as in unbound aggregates in the subretinal space (arrowhead). This demonstrates that biotin linked quantum dots bind to human retinal photoreceptors when injected into an eye bank specimen. This has practical implications in the area of neural prosthetics and neural protection for targeted delivery of drugs, molecules, and electric current to photoreceptors in disease states.

The present invention has been described above with reference to exemplary embodiments. Those skilled in the art having read this disclosure will recognize that changes and modifications may be made to the embodiments without departing from the scope of the invention. These and other changes or modifications are intended to be included within the scope of the present invention.

We claim:

1. A method for increasing electrical activity within an eye, the method comprising:
   implanting within the eye a biocompatible solution of a plurality of quantum dots, at least one of the plurality of quantum dots further comprising a bio-targeted coating comprising biotin,
   wherein the bio-targeted coating adheres directly to a targeted retinal cell and maintains the at least one of the plurality of quantum dots in close interaction with the targeted retinal cell for an extended period of time,
   wherein, when light enters the eye, the at least one of the plurality of quantum dots emits an electrical potential, thereby increasing electrical activity in a damaged retina comprising the targeted retinal cell, and
   wherein the increase improves the function of the damaged retina.

2. The method of claim 1, wherein the implanting includes implanting the plurality of quantum dots within a vitreous portion of the eye.

3. The method of claim 1, wherein the implanting includes implanting the plurality of quantum dots within a sub-retinal portion of the eye.

4. The method of claim 1, wherein the targeted retinal cell is a photoreceptor cell.

5. The method of claim 1, wherein the targeted retinal cell is a sub-retinal cell.

6. The method of claim 1, wherein the at least one of the plurality of quantum dots comprises a core formed of CdSe and a shell formed of ZnS.

7. The method of claim 1, wherein the plurality of quantum dots fluoresces a plurality of colors.

8. The method of claim 1, wherein the plurality of quantum dots emits a variety of electrical potentials in response to light of multiple wavelengths.

9. A photoactive device for stimulating electrical activity within an eye with retinal damage comprising:
   a biocompatible solution of a plurality of quantum dots, at least one of the plurality of quantum dots further comprising a biotin coating,
   wherein the biotin coating is configured to adhere directly to a targeted retinal cell and maintain the at least one of the plurality of quantum dots in close interaction with the targeted retinal cell for an extended period of time,
   wherein, after the biocompatible solution is implanted within the eye and light enters the eye, the at least one of the plurality of quantum dots emits an electrical potential, thereby increasing electrical activity in a damaged retina comprising the targeted retinal cell, and
   wherein the increase improves the function of the damaged retina.

10. The photoactive device of claim 9, wherein the targeted retinal cell is a sub-retinal cell.

11. The photoactive device of claim 9, wherein the at least one of the plurality of quantum dots comprises a core formed of CdSe and a shell formed of ZnS.

12. The photoactive device of claim 9, wherein the plurality of quantum dots fluoresces a plurality of colors.

13. The photoactive device of claim 9, wherein the plurality of quantum dots emits a variety of electrical potentials in response to light of multiple wavelengths.

* * * * *

UNITED STATES PATENT AND TRADEMARK OFFICE
CERTIFICATE OF CORRECTION

PATENT NO. : 9,144,608 B2
APPLICATION NO. : 14/249079
DATED : September 29, 2015
INVENTOR(S) : Jeffrey Olson and Naresh Mandava It is certified that error appears in the above-identified patent and that said Letters Patent is hereby corrected as shown below:

TITLE PAGE

Item (71), please delete "Colorado," and insert therefor --Colorado, a body corporate,--.

Item (73), please delete "Colorado," and insert therefor --Colorado, a body corporate,--.

Signed and Sealed this
Twenty-eighth Day of June, 2016

Michelle K. Lee
*Director of the United States Patent and Trademark Office*